(12) United States Patent
Tsujita

(10) Patent No.: US 8,650,960 B2
(45) Date of Patent: Feb. 18, 2014

(54) METHOD AND APPARATUS FOR IMAGING BIOLOGICAL DATA

(75) Inventor: Kazuhiro Tsujita, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 328 days.

(21) Appl. No.: 13/067,764

(22) Filed: Jun. 24, 2011

(65) Prior Publication Data

US 2011/0314921 A1    Dec. 29, 2011

(30) Foreign Application Priority Data

Jun. 24, 2010    (JP) .................................. 2010-143375

(51) Int. Cl.
*G01H 9/00* (2006.01)

(52) U.S. Cl.
USPC ............................................. 73/657; 73/649

(58) Field of Classification Search
USPC .............................. 73/657, 649, 655; 356/432
See application file for complete search history.

(56) References Cited

U.S. PATENT DOCUMENTS

| | | | |
|---|---|---|---|
| 5,995,223 A * | 11/1999 | Power | 356/495 |
| 6,615,072 B1 * | 9/2003 | Izatt et al. | 600/478 |
| 6,709,393 B2 * | 3/2004 | Ogawa | 600/443 |
| 7,245,789 B2 * | 7/2007 | Bates et al. | 385/7 |
| 7,787,121 B2 * | 8/2010 | Tsujita et al. | 356/407 |
| 7,864,307 B2 * | 1/2011 | Fukutani et al. | 356/73 |
| 7,916,283 B2 * | 3/2011 | Fukutani et al. | 356/73 |
| 8,016,419 B2 * | 9/2011 | Zhang et al. | 351/206 |
| 8,300,224 B2 * | 10/2012 | Nakajima et al. | 356/432 |

FOREIGN PATENT DOCUMENTS

JP    2005-021380    1/2005

* cited by examiner

*Primary Examiner* — J M Saint Surin
(74) *Attorney, Agent, or Firm* — Jean C. Edwards; Edwards Neils PLLC

(57) ABSTRACT

An imaging apparatus for generating photoacoustic images and ultrasound images that is capable of generating both types of images with high resolution is provided. An ultrasound probe includes a plurality of probe elements. A first phase matching adding section reads out photoacoustic signals from a photoacoustic element data memory, and administers phase matching addition within a first phase matching range. An image processing section generates a photoacoustic image based on phase matched and added data. A second phase matching adding section administers phase matching addition on reflected acoustic signals sampled by a signal obtaining section within a second phase matching range. An image processing section generates an ultrasound image based on phase matched and added data. The first phase matching range is greater than the second phase matching range.

20 Claims, 5 Drawing Sheets

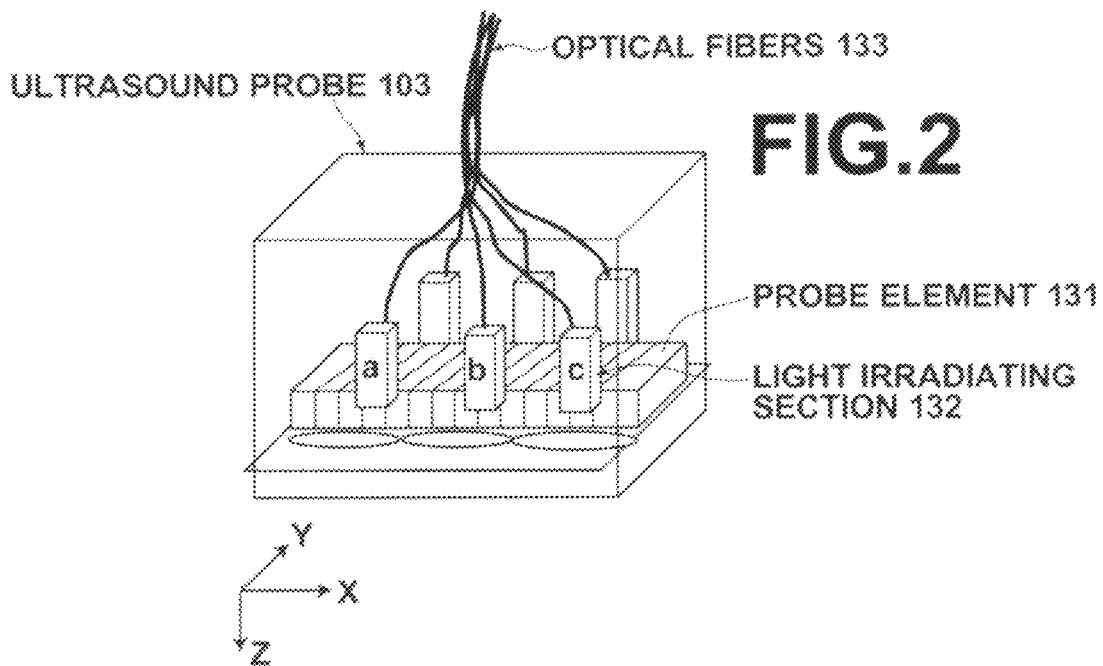
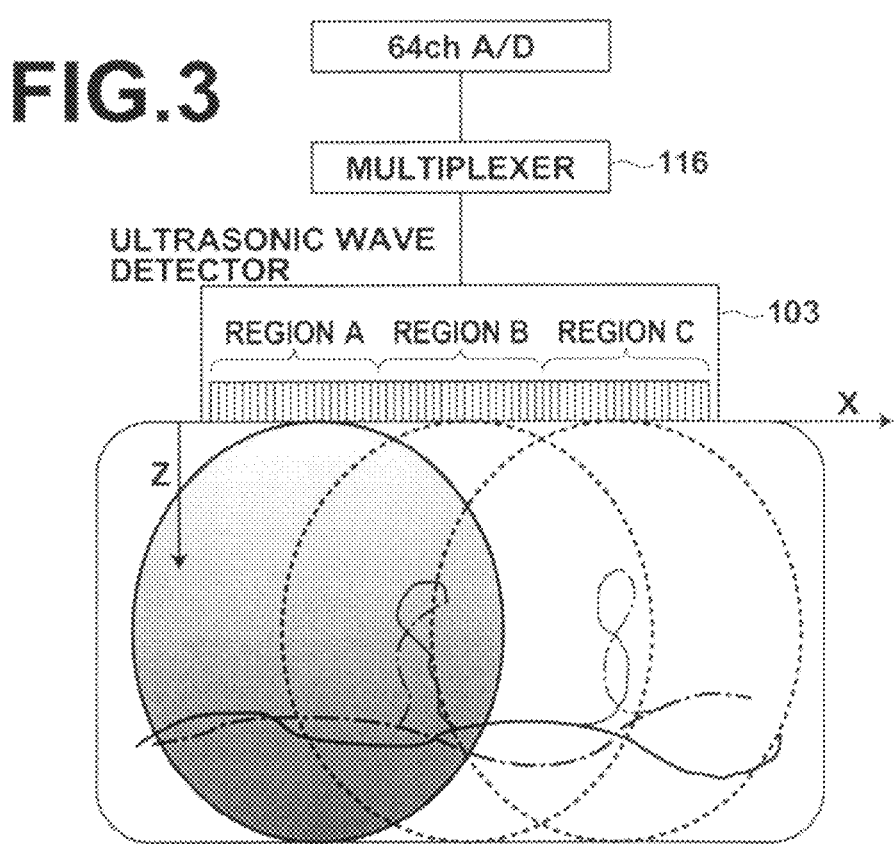

METHOD AND APPARATUS FOR IMAGING BIOLOGICAL DATA

CROSS-REFERENCE TO RELATED APPLICATIONS

The present application claims priority from Japanese Patent Application No. 2010-143375, filed Jun. 24, 2010, the contents of which are herein incorporated by reference in their entirety.

BACKGROUND OF THE INVENTION

1. Field of the Invention

The present invention is related to an imaging apparatus. More specifically, the present invention is related to an imaging apparatus and a biological data imaging method that irradiates light onto a subject, obtains images based on acoustic signals which are generated accompanying the irradiation of light, emits ultrasonic waves into the subject, and obtains images based on the reflected ultrasonic waves.

2. Description of the Related Art

The ultrasound examination method is known as a method that enables non destructive examination of the states of the interiors of examination targets. Ultrasound examinations employ ultrasound probes which are capable of outputting and detecting ultrasonic waves. When ultrasound probes are placed in contact with examination targets and ultrasonic waves are generated, the ultrasonic waves propagate within the interiors of the examination targets, and are reflected when they reach hard objects. The ultrasound probes detect the reflected acoustic waves, and distances are calculated based on the time for the reflected waves to reach the ultrasound probe, to enable visualization of the interiors of the examination targets as images.

Photoacoustic imaging is also known as a method for imaging the interiors of living organisms by utilizing the photoacoustic effect. Generally, in photoacoustic imaging, pulsed laser beams such as laser pulses are irradiated into the living organisms. Biological tissue that absorbs the energy of the pulsed laser beams generate ultrasonic waves (photoacoustic signals) by volume expansion thereof due to heat. The photoacoustic signals are detected by an ultrasound probe or the like, and the detected signals are analyzed, to enable visualization of the living organisms based on ultrasonic waves.

Japanese Unexamined Patent Publication No. 2005-21380, for example, discloses an apparatus that generates and displays ultrasound images and photoacoustic images. When generating an ultrasound image, the apparatus outputs ultrasonic waves into the interior of an organism from probe elements of an ultrasound probe. Reflected acoustic waves, that is, the reflected ultrasonic waves, are detected by adjacent probe elements of a predetermined number of channels. The detected reflected acoustic waves are phase matched and added, to enable specification of the depth positions within the organism at which the ultrasonic waves were reflected. The output of ultrasonic waves and detection of reflected acoustic waves are repeatedly executed while shifting the probe element corresponding to single channels (single lines), to construct the ultrasound image.

Meanwhile, when generating a photoacoustic image, light from a light source is guided to biological tissue by a waveguide section, and a pulsed laser light beam is irradiated onto the biological tissue. After irradiation of the pulsed laser beam, photoacoustic signals are detected by the adjacent probe elements of a predetermined number of channels of the ultrasound probe in a manner similar to that during generation of the ultrasound image. The detected photoacoustic signals are phase matched and added, to enable specification of the depth positions within the organism at which the photoacoustic signals are generated. The irradiation of the pulsed laser beam and the detection of the photoacoustic waves are repeatedly executed while shifting the probe element corresponding to single channels (single lines), to construct the photoacoustic image.

Here, the phase matching addition process is a common process in both generation of the ultrasound image and generation of the photoacoustic image. In phase matching addition in the two types of image generation, reflected acoustic waves and photoacoustic signals which have been sampled in parallel by respective sampling circuits are input, the input reflected acoustic waves and photoacoustic signals are respectively phase matched and added. Generally, the number of pieces of data (number of channels) capable of being sampled in parallel by sampling circuits is less than the number of probe elements provided on an ultrasound probe. For example, the total number of probe elements of an ultrasound probe is 128, and a sampling circuit is capable of sampling data corresponding to 64 channels in parallel. In this case, data from 64 probe elements are respectively phase matched and added to generate the ultrasound image and the photoacoustic image.

How to set the range of phase matching when generating ultrasound images and photoacoustic images in apparatuses which are capable of generating both types of images had not heretofore been discussed. The present inventors have found that it was not possible to achieve both high resolution ultrasound images and high resolution photoacoustic images in the case that the phase matching range is the same when generating the two types of images.

SUMMARY OF THE INVENTION

The present invention has been developed in view of the foregoing circumstances. It is an object of the present invention to provide an imaging apparatus and a biological data imaging method, which are capable of generating both ultrasound images and photoacoustic images at high resolution.

In order to achieve the above object, the present invention provides an imaging apparatus, comprising:

a light irradiating section, for irradiating light onto a subject;

an ultrasound probe that includes a plurality of probe elements, each of which is capable of outputting acoustic signals into the subject, detecting photoacoustic signals generated by the subject due to the irradiation of light by the light irradiating section, and detecting reflected acoustic signals which are reflections of the acoustic signals output into the subject;

a first phase matching adding section, for phase matching and adding the photoacoustic signals detected by the probe elements within a first phase matching range;

a first image processing section, for generating a photoacoustic image based on data which has been phase matched and added by the first phase matching adding section;

a second phase matching adding section, for phase matching and adding the reflected acoustic signals detected by the probe elements within a second phase matching range, which is smaller than the first phase matching range; and a second image processing section, for generating an ultrasound image based on data which has been phase matched and added by the second phase matching adding section.

The biological data imaging apparatus of the present invention may further comprise:

a signal obtaining section for sampling the photoacoustic signals and the reflected acoustic signals detected by the probe elements. In this case, the first phase matching adding section phase matches and adds the photoacoustic signals which have been sampled by the signal obtaining section, and the second phase matching adding section phase matches and adds the reflected acoustic signals which have been sampled by the signal obtaining section.

The biological data imaging apparatus of the present invention may further comprise:

a region selecting section, for sequentially selecting partial regions from among a plurality of partial regions into which a range of the subject to be imaged is divided. In this case, the light irradiating section irradiates light onto a range that includes at least the selected partial region, the signal obtaining section samples photoacoustic signals detected by probe elements corresponding to the selected partial region and stores the sampled photoacoustic signals into a photoacoustic element data memory, and the first phase matching adding section reads out the photoacoustic signals detected by the probe elements corresponding to the first phase matching range from the photoacoustic element data memory and performs phase matching addition.

The first phase matching range may be greater than the number of pieces of data capable of being sampled in parallel by the signal obtaining section. The number of probe elements corresponding to each partial region may be less than or equal to the number of pieces of data capable of being sampled in parallel by the signal obtaining section. The width of each partial region may be the width of a region corresponding to the number of probe elements that detect the number of pieces of data capable of being sampled in parallel by the signal obtaining section.

The first phase matching adding section may read out the photoacoustic signals from the photoacoustic element data memory and perform phase matching addition after the region selecting section has selected all of the partial regions, and the signal obtaining section has sampled the photoacoustic signals detected by the probe elements of the range of the subject to be imaged and has stored the sampled photoacoustic signals in the photoacoustic element data memory.

The second phase matching range may be equal to the width of the number of pieces of data capable of being sampled in parallel by the signal obtaining section.

The probe elements of the ultrasound probe may output acoustic signals into a predetermined range of the subject while sequentially shifting an output range;

the signal obtaining section may sample reflected acoustic signals detected by probe elements corresponding to the ranges into which the acoustic signals have been output, and store the sampled reflected acoustic signals into an ultrasound element data memory; and the second phase matching adding section may read out the reflected acoustic signals detected by the probe elements corresponding to the second phase matching range from the ultrasound element data memory and perform phase matching addition.

In this case, the second phase matching adding section may read out the reflected acoustic signals from the ultrasound element data memory and perform phase matching addition after the ultrasound probe has output acoustic signals into a range of the subject to be imaged, and the signal obtaining section has sampled the reflected acoustic signals detected by the probe elements of the range of the subject to be imaged and has stored the sampled reflected acoustic signals in the ultrasound element data memory.

Instead of the above configuration, the probe elements of the ultrasound probe may output acoustic signals into a predetermined range of the subject while sequentially shifting an output range;

the signal obtaining section may sample reflected acoustic signals detected by probe elements corresponding to the ranges into which the acoustic signals have been output; and the second phase matching adding section may perform phase matching addition of the reflected acoustic signals which have been sampled in parallel by the signal obtaining section.

In order to achieve the above object, the present invention provides an imaging method, comprising the steps of:

irradiating light onto a subject;

employing an ultrasound probe that includes a plurality of probe elements to detect photoacoustic signals generated by the subject due to the irradiated light;

phase matching and adding the photoacoustic signals detected by the probe elements within a first phase matching range;

generating a photoacoustic image based on the phase matched and added photoacoustic signals;

outputting acoustic signals into the subject;

employing the ultrasound probe to detect reflected acoustic signals which are reflections of the acoustic signals output into the subject;

phase matching and adding the reflected acoustic signals detected by the probe elements within a second phase matching range, which is smaller than the first phase matching range; and generating an ultrasound image based on the phase matched and added reflected acoustic signals.

In the biological data imaging apparatus and the biological data imaging method of the present invention, the photoacoustic signals detected by the probe elements of the ultrasound probe are phase matched and added within the first phase matching range, and the reflected acoustic signals detected by the probe elements are phase matched and added within the second phase matching range which is narrower than the first phase matching range. Two types of images both having high resolution can be generated by causing the first phase matching range to be wider than the second phase matching range, according to the detection properties of the photoacoustic signals and the detection properties of the ultrasonic wave signals.

BRIEF DESCRIPTION OF THE DRAWINGS

FIG. 2 is a perspective view that illustrates an ultrasound probe.

FIG. 3 is a diagram that schematically illustrates the ultrasound probe and a subject during generation of a photoacoustic image.

DESCRIPTION OF THE PREFERRED EMBODIMENTS

Figure 1:
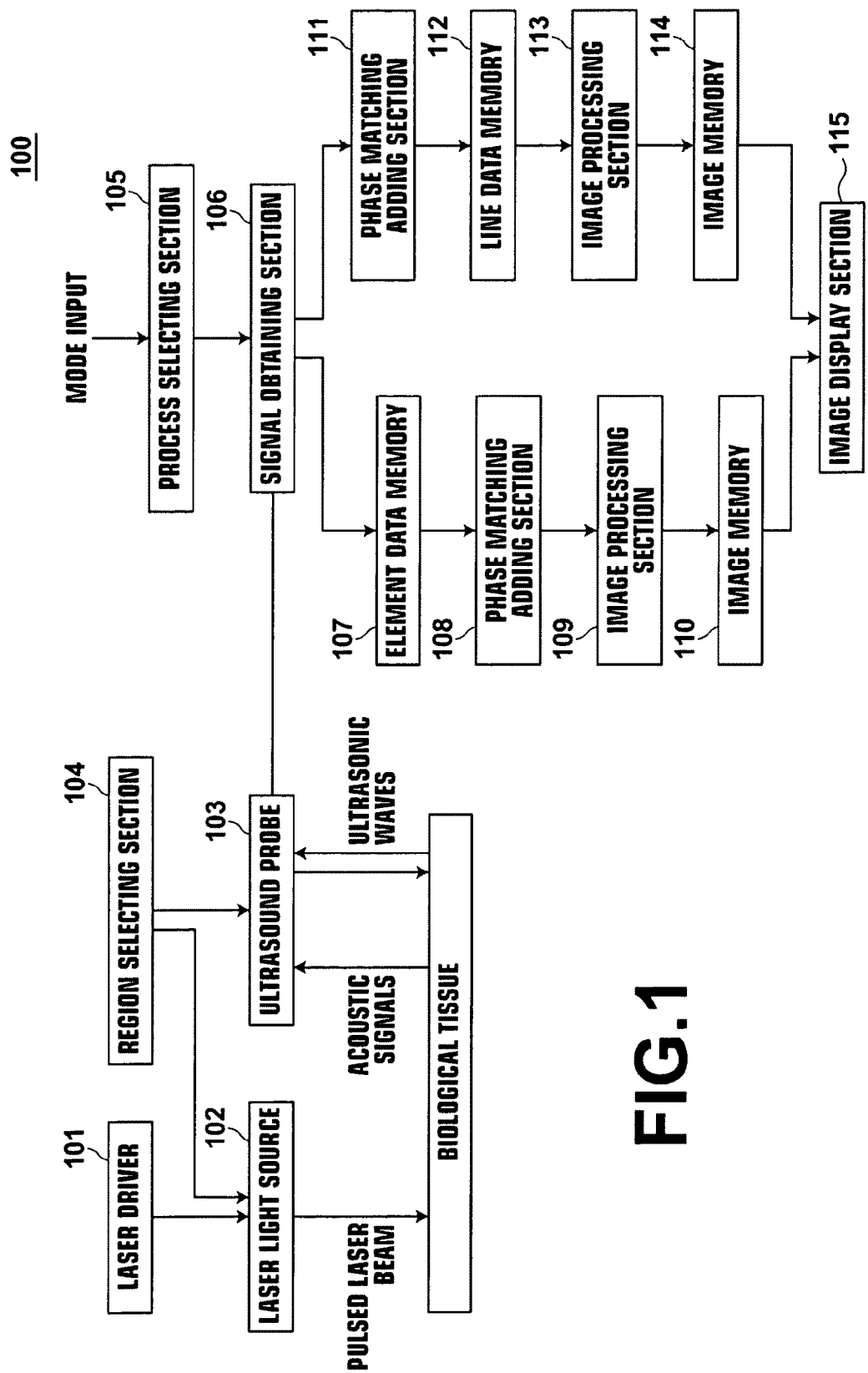
FIG. 1 is a block diagram that illustrates an imaging apparatus according to a first embodiment of the present invention.

Hereinafter, embodiments of the present invention will be described in detail with reference to the attached drawings. FIG. 1 is a block diagram that illustrates an imaging apparatus 100 according to a first embodiment of the present invention. The biological data imaging apparatus 100 is equipped with: a laser driver 101; a laser light source 102; an ultrasound probe 103; a region selecting section 104; a process selecting section 105; a signal obtaining section 106; a photoacoustic element data memory 107; a first phase matching adding section 108; a first image processing section 109; an image memory 110; a second phase matching adding section 111; a line data memory 112; a second image processing section 113; an image memory 114; and an image display section 115.

The laser driver 101 drives the laser light source 102. The laser light source 102 outputs a pulsed laser beam to biological tissue, which is a target of examination, when generating photoacoustic images. A Q switch solid state laser, for example, may be employed as the laser light source 102. Trigger signals are input to the laser driver 101, and the laser driver 101 drives the laser light source 102 in response to the trigger signals.

The ultrasound probe 103 is equipped with ultrasound probe elements corresponding to a plurality of channels. The probe elements are provided corresponding to ranges of the biological tissue to be imaged. For example, the ultrasound probe 103 is equipped with 192 probe elements. Each probe element is capable of outputting ultrasonic waves (acoustic signals) into the biological tissue. The ultrasound probe 103 detects ultrasonic waves (hereinafter, also referred to as "photoacoustic signals") which are generated within the biological tissue by the pulsed laser beam being irradiated thereon. In addition, the ultrasound probe 103 detects acoustic waves (hereinafter, also referred to as "reflected acoustic signals") which are the output ultrasonic waves reflected by the biological tissue. Each probe element converts the detected photoacoustic signals and the reflected acoustic signals into electric signals, and outputs the electric signals.

The signal obtaining section 106 samples the electric signals output by the ultrasound probe 106. That is, the signal obtaining section 106 samples the photoacoustic signals and the reflected acoustic signals detected by the probe elements of the ultrasound probe 103. The signal obtaining section 106 samples the electric signals output by the ultrasound probe a plurality of times over a predetermined measurement period. The signal obtaining section 106 includes a preamplifier for amplifying fine signals and an A/D converter for converting analog signals into digital signals, for example. The number of signals (number of channels) capable of being sampled in parallel by the signal obtaining section 106 is less than the total number of probe elements (total number of channels) of the ultrasound probe 103. For example, in the case that the ultrasound probe 103 is equipped with 192 probe elements, the number of channels capable of being sampled in parallel by the signal obtaining section 106 is 64.

The process selecting section 105 selects one of photoacoustic image generation and ultrasound image generation. When the process selecting section 105 has selected photoacoustic image generation, the signal obtaining section 106 stores sampled photoacoustic signals corresponding to a predetermined number of channels in the photoacoustic element data memory 107. When the process selecting section 105 has selected ultrasound image generation, the signal obtaining section 106 outputs sampled reflected acoustic signals corresponding to a predetermined number of channels to the second phase matching adding section 111.

The range (the range of the biological tissue to be imaged) corresponding to the plurality of probe elements of the ultrasound probe 103 is divided into a plurality of partial regions related to photoacoustic signal generation. When the process selecting section 105 has selected photoacoustic image generation, the region selecting section 104 selects one of the partial regions. For example, the range to be imaged of the biological tissue is divided into three partial regions, Region A, Region B, and Region C. Region A, Region B, and Region C do not overlap with each other. The width of each partial region is the width of a region corresponding to the number of probe elements that detect the number of pieces of data capable of being sampled in parallel by the signal obtaining section 106. For example, in the case that the signal obtaining section 106 is capable of sampling data for 64 channels, the width of each of the partial regions Region A, Region B, and Region C is a width corresponding to 64 probe elements.

The region selecting section 104 notifies the laser driver 101 and the ultrasound probe 103 selection data regarding a selected partial region. The laser driver 101 drives the laser light source 102 such that a pulsed laser beam is irradiated onto a range that includes at least the selected partial region. Meanwhile, the ultrasound probe 103 employs a multiplexer (not shown) or the like to connect the probe elements corresponding to the selected partial region and the signal obtaining section 106. After light is irradiated onto the partial region, the signal obtaining section 106 samples photoacoustic signals detected by the probe elements connected thereto a plurality of times over a predetermined measurement period, and stores the sampled photoacoustic signals in the photoacoustic element data memory 107.

After the sampled data of the photoacoustic signals from the probe elements corresponding to the selected partial region are stored in the photoacoustic element data memory 107, the region selecting section 104 selects a next partial region. The region selecting section 104 sequentially selects the partial regions until the entire range to be imaged of the biological tissue is selected. Sampled data of the photoacoustic signals output by all of the probe elements of the ultrasound probe 103 are stored in the photoacoustic element data memory 107 by the region selecting section 104 sequentially selecting the partial regions. For example, the region selecting section 104 may sequentially select Region A, Region B, then Region C, and the signal obtaining section 106 may sample photoacoustic signals for 64 channels for each region a plurality of times. Thereby, sampled data of photoacoustic signals corresponding to a total of 192 channels are stored in the photoacoustic element data memory 107.

The first phase matching adding section 108 phase matches and adds the photoacoustic signals detected by the probe elements of the ultrasound probe 103 within a first phase matching range. The first phase matching adding section 108 reads out sampled data of the photoacoustic signals within the first phase matching range from the photoacoustic element data memory 107 and performs phase matching addition. The first phase matching range is greater (wider) than the number of pieces of data which are capable of being sampled in parallel by the signal obtaining section 106. The first phase matching adding section 108 reads out the sampled data of the photoacoustic signals from the photoacoustic element data memory 107 and performs phase matching addition after the region selecting section 104 has selected all of the partial regions, and the signal obtaining section 106 has sampled the photoacoustic signals detected by the probe elements of the range of the biological tissue to be imaged and has stored the sampled photoacoustic signals in the photoacoustic element data memory 107.

The first image processing section generates a photoacoustic image based on data which has been phase matched and added by the first phase matching adding section 108. The functions of the first image processing section 109 can be realized by a computer operating according to a predetermined program. Alternatively, the functions of the first image processing section 109 may be realized by a DSP (Digital Signal Processor), an FPGA (Field Programmable Gate Array), or the like. The first image processing section 109 stores the generated photoacoustic image in the image memory 110.

The second phase matching adding section 111 phase matches and adds the reflected acoustic signals detected by the probe elements of the ultrasound probe 103 within a second phase matching range. The second phase matching adding section 111 phase matches and adds the reflected acoustic signals which have been sampled in parallel by the signal obtaining section 106. That is, the second phase matching range is equal to the number of pieces of data capable of being sampled in parallel by the signal obtaining section 106. When ultrasound image generation has been selected by the process selecting section 105, the ultrasound probe 103 outputs acoustic signals from the probe elements into a predetermined range of the biological tissue, while sequentially shifting the output range thereof. The signal obtaining section 106 samples reflected acoustic signals detected by probe elements corresponding to the range into which the acoustic signals have been output, and outputs the sampled reflected acoustic signals to the second phase matching adding section 111. The second phase matching adding section 111 phase matches and adds the reflected acoustic signals output by the signal obtaining section 106.

The second phase matching adding section 111 stores the results of phase matching addition into the line data memory 112. The second image processing section 113 reads out data from the line data memory 112, and generates an ultrasound image based on based on data which has been phase matched and added by the second phase matching adding section 111. The functions of the second image processing section 113 can be realized by a computer operating according to a predetermined program. Alternatively, the functions of the second image processing section 113 may be realized by a DSP, an FPGA, or the like. The second image processing section 113 stores the generated photoacoustic image in the image memory 114.

The image display section 115 reads out the photoacoustic image from the image memory 110 and displays the read out photoacoustic image on a display monitor or the like. In addition, the image display section 115 reads out the ultrasound image from the image memory 114, and displays the read out ultrasound image on the display monitor or the like. The image display section 115 may simultaneously display the photoacoustic image and the ultrasound image on the display monitor or the like. At this time, the photoacoustic image and the ultrasound image may be displayed overlapping each other.

FIG. 2 illustrates the ultrasound probe 103. The ultrasound probe 103 is equipped with the plurality of probe elements 131. The probe elements 131 are arranged unidirectionally along a predetermined direction, for example. Optical fibers 133 guide light output by the laser light source 102 to light irradiating sections 132 provided within the ultrasound probe 103. The light irradiating sections 132 irradiated the pulsed laser beam output by the laser light source 102 onto regions that at least include a selected partial region. The light irradiating sections 132 are provided corresponding to each of Region A, Region B, and Region C, for example. In this case, the light irradiating section 132 corresponding to Region A irradiates the pulse laser beam onto at least Region A when Region A is selected. The light irradiating section 132 corresponding to Region B irradiates the pulse laser beam onto at least Region B when Region B is selected, and the light irradiating section 132 corresponding to Region C irradiates the pulse laser beam onto at least Region C when Region C is selected.

FIG. 3 is a diagram that schematically illustrates the ultrasound probe 103 and the biological tissue during generation of a photoacoustic image. The ultrasound probe 103 is equipped with probe elements 131 (refer to FIG. 2) for 192 channels, for example. The width corresponding to the probe elements 131 is divided into three partial regions (Regions A through C) related to photoacoustic image generation, and the width of each partial region is a width that corresponds to probe elements 131 for 64 channels. If the width of the biological tissue corresponding to the probe elements 131 for 192 channels is 57.6 mm, the width of each partial region will be 19.2. The biological data imaging apparatus 100 performs irradiation of light onto and data collection from the 19.2 mm wide partial regions divided as illustrated in FIG. 3 three times, to obtain data for all 192 channels.

The signal obtaining section 106 includes an A/D converter capable of sampling data for 64 channels in parallel. A multiplexer 116 selectively connects the probe elements of the ultrasound probe 103 and the signal obtaining section 106. The multiplexer 116 is connected to the probe elements corresponding to 192 channels, for example, and selectively connects 64 channels to the A/D converter of the signal obtaining section 106. For example, when Region A is selected, the multiplexer 116 connects the probe elements of the 64 channels corresponding to Region A to the AD converter of the signal obtaining section 106. When Region B is selected, the multiplexer 116 connects the probe elements of the 64 channels corresponding to Region B to the AD converter of the signal obtaining section 106, and when Region C is selected, the multiplexer 116 connects the probe elements of the 64 channels corresponding to Region C to the AD converter of the signal obtaining section 106.

If Region A is selected, and the light irradiating section 132 irradiates a pulsed laser beam onto Region A of the biological tissue, the laser beam propagates with a certain degree of spread due to scattering within the biological tissue. Absorbers such as blood that exist within the biological tissue absorb the energy of the pulsed laser beam, and generate acoustic signals. The amount of time required before these acoustic signals are detected by the probe elements is determined according to the positional relationship between the acoustic signal generation point and the probe elements in the X direction, and the position of the acoustic signal generating point in the Z direction. Electric signals output by the probe elements 131 selected by the multiplexer 116 are sampled a plurality of times over a predetermined measurement period, in order to detect these acoustic signals. Acoustic signals are detected for Region B and Region C in a similar manner, by irradiating a pulsed laser beam onto these regions, and by sampling electric signals output by probe elements corresponding to each of the regions over a predetermined measurement period.

Data necessary to generate a photoacoustic image can be stored in the photoacoustic element data memory 107 by performing photoacoustic signal data collection as described above. The sampled data of the photoacoustic signals stored in the photoacoustic element data memory 107 are phase matched and added by the first phase matching adding section 108. The results of phase matched addition are employed to perform image construction by the first image processing section 109 to obtain a photoacoustic image.

Figure 4:
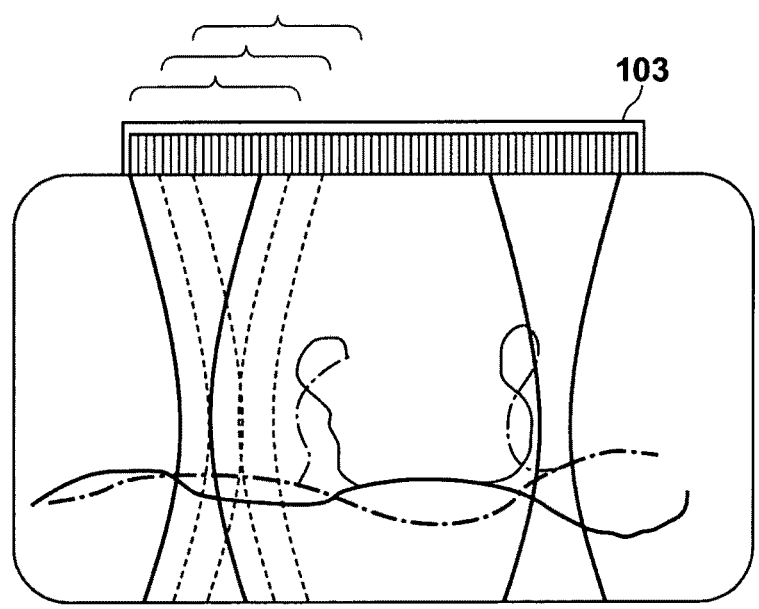
FIG. 4 is a diagram that schematically illustrates the ultrasound probe and a subject during generation of an ultrasound image.

FIG. 4 is a diagram that schematically illustrates the ultrasound probe and biological tissue during generation of an ultrasound image. Note that although omitted from FIG. 4, the ultrasound probe 103 is connected to the signal obtaining section 106 via the multiplexer 116 as in FIG. 3. The number of probe elements provided in the ultrasound probe 103 is 194 channels, as in the case of FIG. 3. In addition, the signal obtaining section 106 includes an A/D converter capable of sampling data for 64 channels in parallel.

During generation of an ultrasound image, the multiplexer 116 selectively connects adjacent probe elements corresponding to 64 channels, from among the probe elements corresponding to 192 channels, to the A/D converter of the signal obtaining section 106. After output of acoustic signals, detection of reflected acoustic signals, and phase matching addition by the second phase matching adding section 111 are complete, the multiplexer 116 shifts the selected probe elements by a single channel, for example. For example, at first, the multiplexer 116 connects 64 probe elements corresponding to a first through 64th channel to the signal obtaining section 106. The second phase matching adding section 111 phase matches and adds reflected acoustic signals detected by the 64 probe elements corresponding to a first through 64th channel. Next, the multiplexer 116 connects probe elements corresponding to a second through 65th channel to the signal obtaining section 106, and the second phase matching adding section 111 phase matches and adds reflected acoustic signals detected by these 64 probe elements.

Data collection with respect to the reflected acoustic signals as described above is performed over the entire range of the probe elements, while sequentially shifting the selected probe elements 1 channel at a time. The acoustic signals are output and the reflected acoustic signals are detected across the entire range of the probe elements corresponding to 192 channels, and phase matching addition is performed for all of the reflected acoustic signals. Thereby, data necessary to generate the ultrasound image can be stored in the line data memory 112 (refer to FIG. 1). The second image processing section reads out the results of phase matching addition from the line data memory 112 and performs image construction to obtain the ultrasound image.

Figure 5:
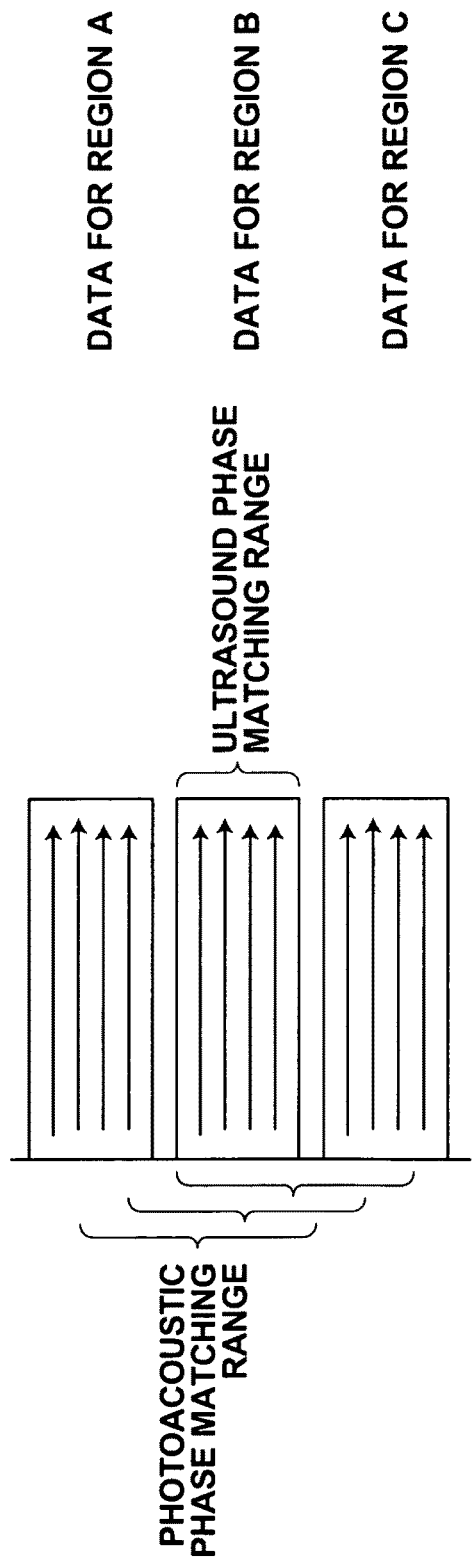
FIG. 5 is a block diagram that illustrates pieces of data which are stored in a photoacoustic element data memory.

FIG. 5 is a block diagram that illustrates pieces of data which are stored in the photoacoustic element data memory 107. The sampling initiation time for each region is defined as t=0. A first sampling operation is performed at t=0, and the signal obtaining section 106 performs n sampling operations at a predetermined sampling rate during a sampling period. Thereby, the signal obtaining section 106 samples n photoacoustic signals between a time t=0 and t=n−1. The photoacoustic element data memory 107 stores n pieces of sampled data corresponding to the time between t=0 and t=n−1 for each channel.

Assume that the region selecting section 104 sequentially selects Region A, Region B, and Region C when generating a photoacoustic image. In this case, the signal obtaining section 106 first obtains n pieces of sampled data for the probe elements (for example, probe elements corresponding to 64 channels) for Region A, and stores n pieces of sampled data at locations (addresses) within the photoacoustic element data memory 107 corresponding to each timing between t=0 and t=n−1 for Region A. The signal obtaining section 106 obtains n pieces of sampled data from the probe elements corresponding to 64 channels for both Region B and Region C in a similar manner, and stores n pieces of sampled data at locations (addresses) within the photoacoustic element data memory 107 corresponding to each timing between t=0 and t=n−1. The temporal axes within the photoacoustic element data memory 107 may be corrected for each partial region when storing the data, as necessary.

Assume that reflected acoustic signals from probe elements corresponding to 64 channels, which are capable of being sampled in parallel by the signal obtaining section 106, are phase matched and added by the second phase matching adding section 111 for generating an ultrasound image. In this case, the phase matching range (the second phase matching range) to be employed during ultrasound image generation matches the width of each region during photoacoustic image generation. In this respect, the photoacoustic signals are temporarily stored in the photoacoustic element data memory 107, then undergo phase matching addition. Therefore, the phase matching range (the first phase matching range) to be employed during photoacoustic image generation can be wider than the width of each partial region, that is, the number of pieces of data capable of being sampled in parallel by the signal obtaining section 106. Specifically, if the first phase matching range is set to 96 channels, the first phase matching adding section 108 can phase match and add sampled data from the probe elements corresponding to 64 channels of Region B and sampled data from the probe elements corresponding to 32 channels of Region C.

The present inventors empirically evaluated photoacoustic signals and reflected acoustic signals. As a result, the following was discovered. First, when photoacoustic images were considered, photoacoustic signals which are generated by point shaped absorbers spread in all directions, and meaningful signals can be obtained by a wide range of probe elements of the ultrasound probe 103. In contrast, in ultrasound images, the probe elements of the ultrasound probe 103 detect reflected acoustic signals of acoustic signals output by the probe elements themselves. Therefore, even if the reflectors are point shaped, meaningful signals substantially cannot be obtained by probe elements other than those that have output the acoustic signals. That is, reflected acoustic signals have high directional properties, and the degree of spread of reflected acoustic signals is small.

From the above, it is considered that the image resolution improving effects of increasing the number of signals to be phase matched are small when generating ultrasound images. In fact, if phase matching is performed over a wide range, reflected acoustic signals from probe elements in the peripheries will act as noise components, and will reduce image quality. On the other hand, when generating photoacoustic images, photoacoustic signals spread over a wide range, and probe elements of the ultrasound probe 103 over a wide range can obtain meaningful signals. Therefore, improvements in image resolution are enabled by increasing the number of signals to be phase matched. Therefore, in the present embodiment, the phase matching range (the first phase matching range) to be employed when generating photoacoustic images is set to be greater than the phase matching range (the second phase matching range) to be employed when generating ultrasound images. By adopting this configuration, both high resolution photoacoustic images and high resolution ultrasound images can be obtained.

Here, paragraph 0113 of Japanese Unexamined Patent Publication No. 2005-21380 discloses that if light is irradiated onto subjects employing an optical fiber, the irradiated light will propagate straight while maintaining a thin width, and therefore has strong directional properties. In addition, it is disclosed that it is possible to generate photoacoustic images without phase matching and adding received photoacoustic signals. In Japanese Unexamined Patent Publication No. 2005-21380, photoacoustic signals generated within a subject are converted into electric signals by six probe elements, then two of the electric signals are input to a reception delay circuit via a multiplexer. The reception delay circuit causes the input signals to pass therethrough, and an adder combines the photoacoustic signals. However, if the phase matching range to be employed during photoacoustic image generation is set to be narrower than the phase matching range to be employed during ultrasound image generation in this manner, it is actually impossible to improve the resolution of photoacoustic images.

In the present embodiment, the range to be imaged of the biological tissue is divided into the plurality of partial regions. During photoacoustic image generation, the region selecting section 104 sequentially selects the partial regions. Irradiation of light and detection of photoacoustic signals are performed for each partial region, and the sampled photoacoustic signals are stored in the photoacoustic element data memory 107 for each partial region. Circuits for obtaining a great number of pieces of data in parallel and at high speed are expensive. In the case that the range to be imaged is not divided into the partial regions, it will be necessary for the signal obtaining section 106 to obtain a number of signals corresponding to all of the probe elements of the ultrasound probe 103, in order to store the data necessary for photoacoustic image generation into the photoacoustic element data memory 107. In the present embodiment, irradiation of light and detection of photoacoustic signals are performed for each of the partial regions, and it is sufficient for the number of signals which are sampled in parallel by the signal obtaining section 106 to be the greater of the width of a partial region during photoacoustic image generation and the phase matching range (the second phase matching range) during ultrasound image generation. Accordingly, costs can be reduced compared to a case in which the signal obtaining section 106 is configured to obtain a number of signals corresponding to all of the probe elements of the ultrasound probe 103 in parallel.

In the present embodiment, the first phase matching adding section 108 phase matches and adds the photoacoustic signals stored in the photoacoustic element data memory 107 within the first phase matching range. Because the first phase matching adding section 108 performs phase matching addition on the photoacoustic signals stored in the photoacoustic element data memory 107, the first phase matching range does not depend on the number of signals that the signal obtaining section 106 is capable of sampling in parallel. For this reason, if the width of each partial region during photoacoustic image generation is the same as the second phase matching range employed by the second phase matching adding section 111, the signal obtaining section 106 need only be capable of sampling signals corresponding to the second phase matching range in parallel, and it is not necessary for the signal obtaining section 106 to be capable of sampling signals corresponding to the first phase matching range. The second phase matching range is narrower than the first phase matching range. Therefore, the number of signals capable of being sampled by the signal obtaining section 106 in parallel can be kept small. The present embodiment reduces costs compared to cases in which the signal obtaining section 106 is configured to obtain a number of signals corresponding to the probe elements corresponding to the first phase matching range in parallel. At the same time, the first phase matching range is set to be greater than the number of pieces of data capable of being sampled by the signal obtaining section 106, to realize improvements in the resolution of photoacoustic images.

In the present embodiment, when a certain partial region is selected, it is only necessary to irradiate a pulsed laser beam onto at least the selected partial region. That is, it is not necessary to irradiate the entire range of the biological tissue with the laser beam. For example, a pulsed laser beam on the order of nanoseconds is necessary for photoacoustic imaging. A Q switch solid state laser is an example of a light source to be employed to irradiate such a pulsed laser beam. In the case that the pulsed laser beam is to be irradiated onto the entire range of the biological tissue and power of 20 mj/cm$^2$, which is the safety standard of the Q switch solid state laser, is to be obtained, pulsed output of 60 mJ or greater will be necessary, considering the efficiency of optical systems and the irradiation range. This will become a factor in increasing the cost of the apparatus. In the present embodiment, it is possible to irradiate the pulsed laser beam onto each partial region by switching the irradiation range, thereby suppressing the power of the light source. This is advantageous from the viewpoint of cost.

Figure 6:
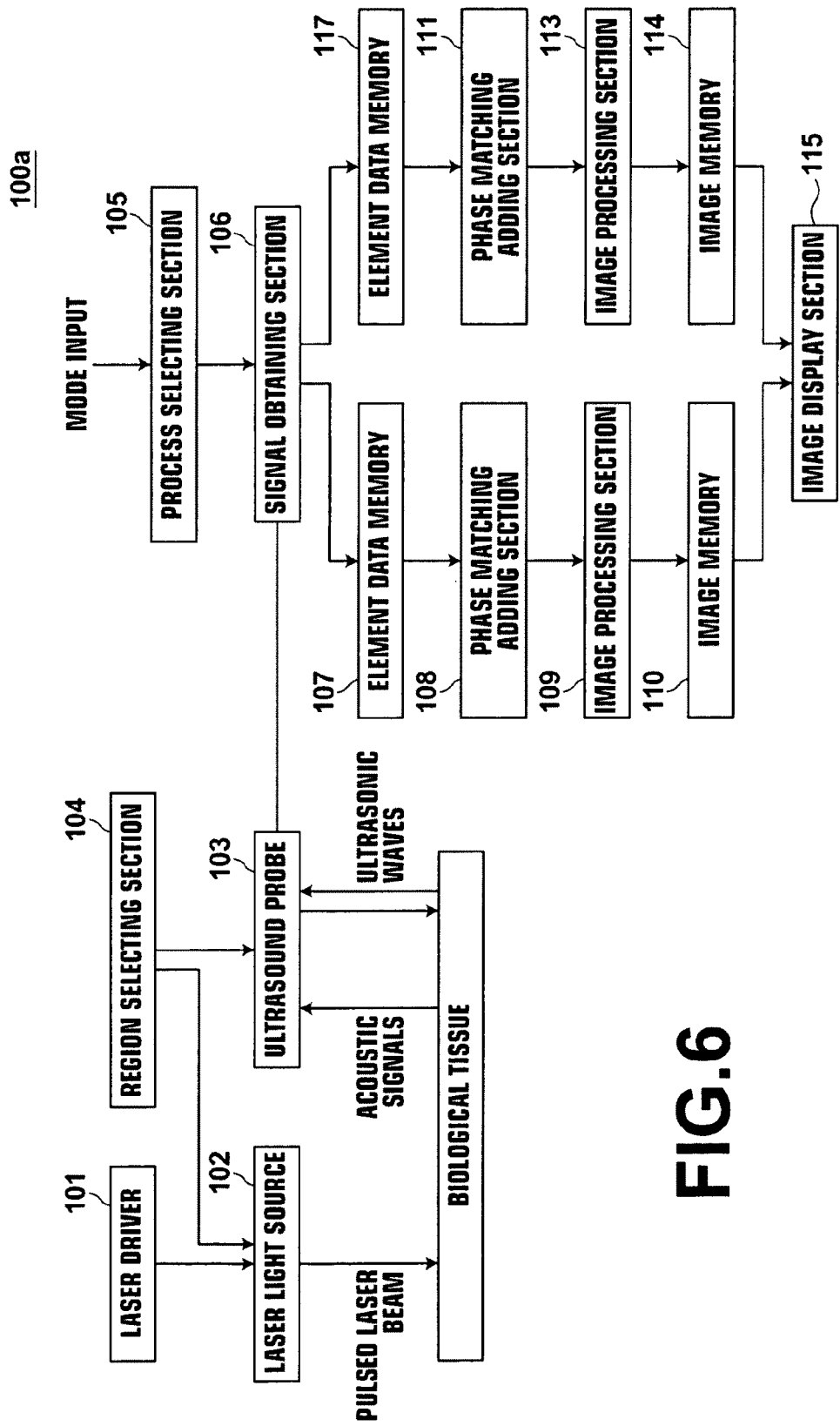
FIG. 6 is a block diagram that illustrates an imaging apparatus according to a second embodiment of the present invention.

Next, a second embodiment of the present invention will be described. FIG. 6 is a block diagram that illustrates an imaging apparatus 100a according to the second embodiment of the present invention. The present embodiment differs from the first embodiment in the ultrasound image generating method. Note that elements which are the same as those of the first embodiment will be denoted with the same reference numerals, and detailed descriptions thereof will be omitted insofar as they are not particularly necessary. Generation of photoacoustic images is performed in the same manner as in the first embodiment. The biological data imaging apparatus 100a is equipped with an ultrasound element data memory 117 instead of the line data memory 112. The ultrasound probe 103 outputs acoustic signals from the probe elements into a predetermined range of the biological tissue, while sequentially shifting the output range thereof. The signal obtaining section 106 samples reflected acoustic signals detected by probe elements corresponding to the range into which the acoustic signals have been output, and stores the sampled reflected acoustic signals in the ultrasound element data memory 117.

The second phase matching adding section 111 reads out the reflected acoustic signals detected by the probe elements corresponding to the second phase matching range from the ultrasound element data memory 117, and performs phase matching addition. The second phase matching adding section 111 reads out the reflected acoustic signals from the ultrasound element data memory 117 and performs phase matching addition after the ultrasound probe 103 has output acoustic signals into a range of the biological tissue to be imaged, and the signal obtaining section 106 has sampled the reflected acoustic signals detected by the probe elements of the range of the biological tissue to be imaged and has stored the sampled reflected acoustic signals in the ultrasound element data memory 117. The second image processing section 113 generates an ultrasound image based on data which has been phase matched and added by the second phase matching adding section 111.

In the present embodiment, data necessary for generating the ultrasound images are stored in the ultrasound element data memory 117, in a manner similar to that when generating a photoacoustic image. Ultrasound images are obtained by the second phase matching adding section 111 administering phase matching addition onto the sampled data of the reflected acoustic signals stored in the ultrasound element data memory 117, and by the second image processing section 113 performing image construction employing the results of phase matching addition. In this case as well, the same advantageous effects as those obtained by the first embodiment, that is, realization of obtainment of both high resolution photoacoustic images and high resolution ultrasound images, can be obtained, by setting the first phase matching range to be greater than the second phase matching range.

Note that in the embodiments described above, the partial regions during photoacoustic image generation are set such that they do not overlap each other. However, the present invention is not limited to such a configuration. The partial regions may include regions that overlap with other partial regions. For example, if the ultrasound probe 103 has probe elements corresponding to 192 channels, the range to be imaged may be divided into five partial regions. The first through 64th probe elements may be designated as Region A, the 32nd through 96th probe elements may be designated as Region B, the 96th through 128th probe elements may be designated as Region C, the 128th through 160th probe elements may be designated as Region D, and the 160th through 192nd probe elements may be designated as Region E. In this case, for example, the 32nd through 64th probe elements overlap between Region A and Region B, and the 64th and 96th probe elements overlap between Region B and Region C.

In the case that the regions overlap as described above, because the 32nd through 64th probe elements overlap between Region A and Region B, for example, data sampled when the pulsed laser beam is irradiated onto Region A and data sampled when the pulsed laser beam is irradiated onto Region B are obtained from the probe elements in the overlapping region. The data of the overlapping regions can enable improvements in S/N ratio, by averaging the plurality of pieces of sampled data, for example. However, as the overlaps among the partial regions increase, the number of pulsed laser beam irradiations and data sampling operations will increase. Therefore, the imaging speed will deteriorate. Whether the partial regions are to have overlapping regions, or the degree of overlap among the partial regions may be set as appropriate according to desired imaging speed and the like.

The present invention has been described based on preferred embodiments thereof. However, the biological data imaging apparatus and the biological data imaging method of the present invention are not limited to the above embodiments. Various modifications and changes may be added to the configurations of the above embodiments, as long as they do not stray from the spirit and scope of the inventions as claimed below.

What is claimed is:

1. An imaging apparatus, comprising:
   a light irradiating section, that irradiates light onto a subject;
   an ultrasound probe that includes a plurality of probe elements, each of which is configured to output acoustic signals into the subject, configured to detect photoacoustic signals generated within the subject due to absorption of the light irradiated by the light irradiating section, and configured to detect reflected acoustic signals which are reflections of the acoustic signals output into the subject;
   a first phase matching adding section that phase matches and adds the photoacoustic signals detected by the probe elements within a first phase matching range;
   a first image processing section that generates a photoacoustic image based on data which has been phase matched and added by the first phase matching adding section;
   a second phase matching adding section that phase matches and adds the reflected acoustic signals detected by the probe elements within a second phase matching range, which is smaller than the first phase matching range; and
   a second image processing section, that generates an ultrasound image based on data which has been phase matched and added by the second phase matching adding section.

2. An imaging apparatus as defined in claim 1, further comprising:
   a signal obtaining section that samples the photoacoustic signals and the reflected acoustic signals detected by the probe elements; and wherein:
   the first phase matching adding section phase matches and adds the photoacoustic signals which have been sampled by the signal obtaining section, and the second phase matching adding section phase matches and adds the reflected acoustic signals which have been sampled by the signal obtaining section.

3. An imaging apparatus as defined in claim 2, further comprising:
   a region selecting section that sequentially selects partial regions from among a plurality of partial regions into which a range of the subject to be imaged is divided; and wherein:
   the light irradiating section irradiates light onto a range that includes at least the selected partial region, the signal obtaining section samples photoacoustic signals detected by probe elements corresponding to the selected partial region and stores the sampled photoacoustic signals into a photoacoustic element data memory, and the first phase matching adding section reads out the photoacoustic signals detected by the probe elements corresponding to the first phase matching range from the photoacoustic element data memory and performs phase matching addition.

4. An imaging apparatus as defined in claim 3, wherein:
   the first phase matching range is greater than the number of pieces of data being sampled in parallel by the signal obtaining section.

5. An imaging apparatus as defined in claim 3, wherein:
   the number of probe elements corresponding to each partial region is less than or equal to the number of pieces of data being sampled in parallel by the signal obtaining section.

6. An imaging apparatus as defined in claim 3, wherein:
   the width of each partial region is the width of a region corresponding to the number of probe elements that detect the number of pieces of data being sampled in parallel by the signal obtaining section.

7. An imaging apparatus as defined in claim 3, wherein:
   the first phase matching adding section reads out the photoacoustic signals from the photoacoustic element data memory and performs phase matching addition after the region selecting section has selected all of the partial regions, and the signal obtaining section has sampled the photoacoustic signals detected by the probe elements of the range of the subject to be imaged and has stored the sampled photoacoustic signals in the photoacoustic element data memory.

8. An imaging apparatus as defined in claim 2, wherein:
the second phase matching range is equal to the number of pieces of data being sampled in parallel by the signal obtaining section.

9. An imaging apparatus as defined in claim 2, wherein:
the probe elements of the ultrasound probe output acoustic signals into a predetermined range of the subject while sequentially shifting an output range;
the signal obtaining section samples reflected acoustic signals detected by probe elements corresponding to the ranges into which the acoustic signals have been output and stores the sampled reflected acoustic signals into an ultrasound element data memory; and
the second phase matching adding section reads out the reflected acoustic signals detected by the probe elements corresponding to the second phase matching range from the ultrasound element data memory and performs phase matching addition.

10. An imaging apparatus as defined in claim 9, wherein:
the second phase matching adding section reads out the reflected acoustic signals from the ultrasound element data memory and performs phase matching addition after the ultrasound probe has output acoustic signals into a range of the subject to be imaged, and the signal obtaining section has sampled the reflected acoustic signals detected by the probe elements of the range of the subject to be imaged and has stored the sampled reflected acoustic signals in the ultrasound element data memory.

11. An imaging apparatus as defined in claim 2, wherein:
the probe elements of the ultrasound probe output acoustic signals into a predetermined range of the subject while sequentially shifting an output range;
the signal obtaining section samples reflected acoustic signals detected by probe elements corresponding to the ranges into which the acoustic signals have been output; and
the second phase matching adding section performs phase matching addition of the reflected acoustic signals which have been sampled in parallel by the signal obtaining section.

12. An imaging method, comprising the steps of:
irradiating light onto a subject;
employing an ultrasound probe that includes a plurality of probe elements to detect photoacoustic signals generated within by the subject due to absorption of the irradiated light;
phase matching and adding the photoacoustic signals detected by the probe elements within a first phase matching range;
generating a photoacoustic image based on the phase matched and added photoacoustic signals;
outputting acoustic signals into the subject;
employing the ultrasound probe to detect reflected acoustic signals which are reflections of the acoustic signals output into the subject;
phase matching and adding the reflected acoustic signals detected by the probe elements within a second phase matching range, which is smaller than the first phase matching range; and
generating an ultrasound image based on the phase matched and added reflected acoustic signals.

13. An imaging method as defined in claim 12, further comprising the step of:
sequentially selecting partial regions from among a plurality of partial regions into which a range of the subject to be imaged is divided; and wherein:
the light irradiating step irradiates light onto a range that includes at least the selected partial region;
the photoacoustic signal detecting step samples photoacoustic signals detected by probe elements corresponding to the selected partial region and stores the sampled photoacoustic signals into a photoacoustic element data memory; and
the phase matching adding step reads out the photoacoustic signals detected by the probe elements corresponding to the first phase matching range from the photoacoustic element data memory and performs phase matching addition.

14. An imaging method as defined in claim 13, wherein:
the first phase matching range is greater than the number of pieces of data being sampled in parallel by the signal obtaining section.

15. An imaging method as defined in claim 13, wherein:
the width of each partial region is the width of a region corresponding to the number of probe elements that detect the number of pieces of data being sampled in parallel by the signal obtaining section.

16. An imaging method as defined in claim 13, wherein:
first phase matching adding step executes readout of the photoacoustic signals from the photoacoustic element data memory and performs phase matching addition after the region selecting section has selected all of the partial regions, and after the sampled photoacoustic signals detected by the probe elements corresponding to the range of the subject to be imaged are stored.

17. An imaging method as defined in claim 13, wherein:
the second phase matching range is equal to the number of pieces of data capable of being sampled in parallel by the signal obtaining section.

18. An imaging method as defined in claim 13, wherein:
the probe elements of the ultrasound probe output acoustic signals into a predetermined range of the subject while sequentially shifting an output range in the acoustic signal outputting step;
the reflected acoustic signal detecting step samples reflected acoustic signals detected by probe elements corresponding to the ranges into which the acoustic signals have been output and stores the sampled reflected acoustic signals into an ultrasound element data memory; and
the phase matching adding step reads out the reflected acoustic signals detected by the probe elements corresponding to the second phase matching range from the ultrasound element data memory and performs phase matching addition.

19. An imaging method as defined in claim 18, wherein:
the reflected acoustic signal phase matching adding step executes phase matching addition after the acoustic signals are output into a range of the subject to be imaged, and the reflected acoustic signals detected by the probe elements of the range of the subject to be imaged are sampled and stored in the ultrasound element data memory.

20. An imaging method as defined in claim 13, wherein:
the probe elements output acoustic signals into a predetermined range of the subject while sequentially shifting an output range;

the reflected acoustic signal detecting step samples reflected acoustic signals detected by probe elements corresponding to the ranges into which the acoustic signals have been output; and the reflected acoustic signal phase matching adding step performs phase matching addition of the reflected acoustic signals which have been sampled in parallel by the signal obtaining section.

* * * * *